US007953611B2

(12) United States Patent
Goodman et al.

(10) Patent No.: US 7,953,611 B2
(45) Date of Patent: May 31, 2011

(54) METHOD OF INCENTIVISING MEMBERS OF A DISEASE MANAGEMENT PROGRAMME TO COMPLY WITH THE PROGRAMME

(75) Inventors: Maurice Ronan Goodman, Gauteng (ZA); Lori Manson, Gauteng (ZA); Craig Nossel, Gauteng (ZA)

(73) Assignee: Discovery Holding Limited, Sandto (ZA)

( * ) Notice: Subject to any disclaimer, the term of this patent is extended or adjusted under 35 U.S.C. 154(b) by 1143 days.

(21) Appl. No.: 09/876,311

(22) Filed: Jun. 7, 2001

(65) Prior Publication Data
US 2002/0055859 A1    May 9, 2002

(30) Foreign Application Priority Data
Sep. 6, 2000  (ZA) .................................... 00/4682

(51) Int. Cl.
*G06Q 50/00* (2006.01)
(52) U.S. Cl. ........ 705/3; 705/2; 705/4; 705/14; 600/300
(58) Field of Classification Search .................. 705/2, 3, 705/14; 600/300
See application file for complete search history.

(56) References Cited

U.S. PATENT DOCUMENTS

| | | |
|---|---|---|
| 4,556,216 A | 12/1985 | Pitkanen |
| 4,699,375 A | 10/1987 | Appelbaum et al. |
| 4,831,526 A | 5/1989 | Luchs et al. |
| 4,837,693 A | 6/1989 | Schotz |
| 4,860,275 A | 8/1989 | Kakinuma et al. |
| 4,975,840 A | 12/1990 | DeTore et al. |
| 5,062,645 A | 11/1991 | Goodman et al. |
| 5,136,502 A | 8/1992 | Van Remortel et al. |
| 5,297,026 A | 3/1994 | Hoffman |
| 5,301,105 A | 4/1994 | Cummings, Jr. |
| 5,324,077 A | 6/1994 | Kessler et al. |
| 5,429,506 A | 7/1995 | Brophy et al. |
| 5,490,260 A | 2/1996 | Miller et al. |
| 5,542,420 A | 8/1996 | Goldman et al. |
| 5,549,117 A * | 8/1996 | Tacklind et al. ............. 600/529 |
| 5,550,734 A | 8/1996 | Tarter et al. |
| 5,574,803 A | 11/1996 | Gaborski et al. |
| 5,631,828 A | 5/1997 | Hagan |
| 5,655,085 A | 8/1997 | Ryan et al. |
| 5,655,997 A | 8/1997 | Greenberg et al. |
| 5,692,501 A | 12/1997 | Minturn |
| 5,722,418 A * | 3/1998 | Bro ................................ 600/545 |
| 5,745,893 A | 4/1998 | Hill et al. |
| 5,752,236 A | 5/1998 | Sexton et al. |
| 5,774,883 A | 6/1998 | Andersen et al. |
| 5,832,467 A | 11/1998 | Wavish |
| 5,867,821 A | 2/1999 | Ballantyne et al. |
| 5,890,129 A | 3/1999 | Spurgeon |
| 5,933,809 A | 8/1999 | Hunt et al. |
| 5,933,815 A | 8/1999 | Golden |
| 5,937,387 A | 8/1999 | Summerell et al. |
| 5,987,434 A | 11/1999 | Libman |
| 5,991,744 A | 11/1999 | Dicresce |
| 6,039,688 A | 3/2000 | Douglas et al. |
| 6,049,772 A | 4/2000 | Payne et al. |
| 6,085,174 A | 7/2000 | Edelman |
| 6,085,976 A | 7/2000 | Sehr ............................... 235/384 |
| 6,108,641 A | 8/2000 | Kenna et al. |
| 6,112,986 A | 9/2000 | Berger et al. |
| 6,151,586 A * | 11/2000 | Brown ........................... 705/14 |
| 6,169,770 B1 | 1/2001 | Henely |
| 6,230,142 B1 | 5/2001 | Benigno et al. |
| 6,338,042 B1 | 1/2002 | Paizis |
| 6,385,589 B1 | 5/2002 | Trusheim et al. |
| 6,513,532 B2 | 2/2003 | Mault et al. |
| 6,587,829 B1 | 7/2003 | Camarda et al. |
| 6,602,469 B1 | 8/2003 | Maus et al. |
| 6,611,815 B1 | 8/2003 | Lewis et al. |
| 6,965,868 B1 | 11/2005 | Bednarek |
| 7,319,970 B1 | 1/2008 | Simone |
| 7,380,707 B1 | 6/2008 | Fredman |
| 7,383,223 B1 | 6/2008 | Dilip et al. |
| 7,624,032 B2 | 11/2009 | Radson |
| 7,630,937 B1 | 12/2009 | Mo et al. |

(Continued)

FOREIGN PATENT DOCUMENTS

AU        2001/276596        3/2003

(Continued)

OTHER PUBLICATIONS

"Sidelines." WWD, p10, Feb 3, 2000.*
Rintelman, Mary Jane, "Choice and cost-savings", Credit Union Management, vol. 19, No. 7, pp. 48, 50. Jul. 1996.
Woodard, Kathy, "Stay healthy for real fun—and profit", Business First-Columbus, vol. 12, No. 19, S.1, p. 13. Jan. 1996.
Spencer, Peter L., "New plan cuts health care costs in half (advantage of health care plan with high deductible)", ; Consumer's Research Magazine, vol. 76, No. 10, pp. 16. Oct. 1993.
U.S. Appl. No. 10/344,176, Non-Final Rejection Dec. 19, 2007.
U.S. Appl. No.10/344,176, Non-Final Rejection Jun. 8, 2009.
U.S. Appl. No. 10/344,176, Response to Office Action May 19, 2008.
U.S. Appl. No. 10/344,176, Response to Office Action Mar. 2, 2009.
U.S. Appl. No. 09/982,274, filed Oct. 17, 2001.
U.S. Appl. No. 09/982,274, Final Rejection Nov. 27, 2006.
U.S. Appl. No. 09/982,274, Final Rejection May 6, 2008.
U.S. Appl. No. 09/982,274, Final Rejection Jun. 9, 2009.
U.S. Appl. No. 09/982,274, Non-Final Rejection Mar. 3, 2006.

(Continued)

*Primary Examiner* — James A Kramer
*Assistant Examiner* — Martin A Gottschalk
(74) *Attorney, Agent, or Firm* — Fleit Gibbons Gutman Bongini & Bianco, PL; Paul D. Bianco; Martin Fleit

(57) ABSTRACT

A method of incentivising members of a disease management program to comply with the program by splitting the program into general program areas and specific program areas. The general program areas are relevant to all of the diseases with which members of the program are stricken while the specific program areas are only relevant to some disease managed by the program. Members of the program are awarded points for taking part in and achieving certain levels within all of the general program areas and within the specific program areas associated with the disease with which they are stricken. The points are accumulated and members are rewarded if their points reach a predetermined level. Furthermore, bonus points are awarded to the members for achieving certain levels in all of the program areas associated with their disease.

9 Claims, No Drawings

U.S. PATENT DOCUMENTS

| | | |
|---|---|---|
| 7,685,007 B1 | 3/2010 | Jacobson |
| 7,797,175 B2 | 9/2010 | Luedtke |
| 2001/0037214 A1 | 11/2001 | Raskin et al. |
| 2002/0002495 A1 | 1/2002 | Ullman |
| 2002/0013717 A1 | 1/2002 | Ando et al. |
| 2002/0016923 A1 | 2/2002 | Knaus |
| 2002/0029158 A1 | 3/2002 | Wolff et al. |
| 2002/0035486 A1 | 3/2002 | Huyn et al. |
| 2002/0038310 A1* | 3/2002 | Reitberg .................. 707/104.1 |
| 2002/0042763 A1 | 4/2002 | Pillay |
| 2002/0049617 A1 | 4/2002 | Lencki et al. |
| 2002/0055859 A1 | 5/2002 | Goodman et al. |
| 2002/0087364 A1 | 7/2002 | Lerner et al. |
| 2002/0103678 A1 | 8/2002 | Burkhalter et al. |
| 2002/0111827 A1 | 8/2002 | Levin et al. |
| 2002/0116231 A1 | 8/2002 | Hele et al. |
| 2002/0138309 A1 | 9/2002 | Thomas |
| 2002/0152097 A1 | 10/2002 | Javors |
| 2002/0184129 A1 | 12/2002 | Arena |
| 2003/0009355 A1 | 1/2003 | Gupta |
| 2003/0028483 A1 | 2/2003 | Sanders et al. |
| 2003/0055767 A1 | 3/2003 | Tamura |
| 2003/0078815 A1 | 4/2003 | Parsons |
| 2003/0120521 A1 | 6/2003 | Sherman |
| 2003/0149596 A1 | 8/2003 | Bost |
| 2003/0200142 A1 | 10/2003 | Hicks et al. |
| 2003/0208385 A1 | 11/2003 | Zander |
| 2003/0233278 A1 | 12/2003 | Marshall |
| 2004/0030625 A1 | 2/2004 | Radson et al. |
| 2004/0059608 A1 | 3/2004 | Gore et al. |
| 2004/0088219 A1 | 5/2004 | Sanders et al. |
| 2004/0267570 A1 | 12/2004 | Becker et al. |
| 2005/0010453 A1 | 1/2005 | Terlizzi |
| 2005/0033609 A1 | 2/2005 | Yang |
| 2005/0038679 A1 | 2/2005 | Short |
| 2005/0060209 A1 | 3/2005 | Hill |
| 2005/0071205 A1 | 3/2005 | Terlizzi |
| 2005/0102172 A1 | 5/2005 | Sirmans, Jr. |
| 2005/0131742 A1 | 6/2005 | Hoffman et al. |
| 2005/0222877 A1 | 10/2005 | Radson et al. |
| 2005/0222878 A1 | 10/2005 | Radson et al. |
| 2005/0228692 A1 | 10/2005 | Hodgdon |
| 2005/0234742 A1 | 10/2005 | Hodgdon |
| 2005/0240449 A1 | 10/2005 | Radson et al. |
| 2005/0256748 A1 | 11/2005 | Gore et al. |
| 2005/0288971 A1 | 12/2005 | Cassandra |
| 2006/0041454 A1 | 2/2006 | Matisonn et al. |
| 2006/0064320 A1 | 3/2006 | Postrel |
| 2006/0074801 A1 | 4/2006 | Pollard et al. |
| 2006/0129436 A1 | 6/2006 | Short |
| 2006/0218011 A1 | 9/2006 | Walker et al. |
| 2007/0050217 A1 | 3/2007 | Holden, Jr. |
| 2007/0112669 A1 | 5/2007 | Wesley |
| 2007/0233512 A1 | 10/2007 | Gore |
| 2008/0154650 A1 | 6/2008 | Matisonn et al. |
| 2008/0189141 A1 | 8/2008 | Gore et al. |
| 2008/0197185 A1 | 8/2008 | Cronin et al. |
| 2008/0255979 A1 | 10/2008 | Slutzky et al. |
| 2008/0262877 A1 | 10/2008 | Hargroder |
| 2008/0312969 A1 | 12/2008 | Raines |
| 2009/0076903 A1 | 3/2009 | Schwarzberg et al. |
| 2009/0150192 A1 | 6/2009 | Gore et al. |
| 2009/0198525 A1 | 8/2009 | Gore et al. |
| 2009/0204441 A1 | 8/2009 | Read |
| 2009/0240532 A1 | 9/2009 | Gore et al. |
| 2009/0259497 A1 | 10/2009 | Gore et al. |
| 2009/0265183 A1 | 10/2009 | Pollard et al. |
| 2009/0299773 A1 | 12/2009 | Gore et al. |
| 2009/0299774 A1 | 12/2009 | Gore et al. |
| 2009/0299775 A1 | 12/2009 | Gore et al. |
| 2009/0299776 A1 | 12/2009 | Gore et al. |
| 2009/0307015 A1 | 12/2009 | Gore et al. |
| 2010/0023354 A1 | 1/2010 | Gore et al. |
| 2010/0023384 A1 | 1/2010 | Pollard et al. |
| 2010/0049541 A1 | 2/2010 | Pollard et al. |

FOREIGN PATENT DOCUMENTS

| | | |
|---|---|---|
| AU | 2005/323847 | 2/2007 |
| AU | 2007/257457 | 1/2009 |
| AU | 2007/257458 | 1/2009 |
| AU | 2007/257546 | 1/2009 |
| AU | 2007/298514 | 2/2009 |
| AU | 2007/301521 | 5/2009 |
| CN | 2005/880047059 | 7/2007 |
| EP | 1050821 | 11/2000 |
| IL | 195735 | 12/2008 |
| IL | 195737 | 12/2008 |
| IL | 195738 | 12/2008 |
| WO | 02/047074 | 6/2002 |
| WO | 03/007230 | 1/2003 |
| WO | 2007/141695 | 12/2007 |
| WO | 2007/141696 | 12/2007 |
| WO | 2007/141968 | 12/2007 |
| WO | 2008/035280 | 3/2008 |
| ZA | 98/02005 | 3/1998 |
| ZA | 98/11943 | 12/1998 |
| ZA | 2000/04682 | 9/2000 |
| ZA | 2004/02587 | 4/2004 |
| ZA | 2004/02891 | 4/2004 |
| ZA | 2004/05935 | 7/2004 |
| ZA | 2004/06294 | 8/2004 |
| ZA | 2006/01934 | 3/2006 |
| ZA | 2006/04673 | 6/2006 |
| ZA | 2006/04674 | 6/2006 |
| ZA | 2006/04687 | 6/2006 |
| ZA | 2006/04688 | 6/2006 |
| ZA | 2006/07789 | 9/2006 |
| ZA | 2006/07992 | 9/2006 |
| ZA | 2008-03529 | 4/2008 |
| ZA | 2008/04807 | 6/2008 |
| ZA | 2008/04808 | 6/2008 |
| ZA | 2008/04809 | 6/2008 |
| ZA | 2008/04810 | 6/2008 |
| ZA | 2008/04811 | 6/2008 |
| ZA | 2009/01740 | 3/2009 |

OTHER PUBLICATIONS

U.S. Appl. No. 09/982,274, Non-Final Rejection Aug. 9, 2007.
U.S. Appl. No. 09/982,274, Non-Final Rejection Oct. 17, 2008.
U.S. Appl. No. 09/982,274, Response to Office Action Sep. 6, 2006.
U.S. Appl. No. 09/982,274, Response to Office Action May 29, 2007.
U.S. Appl. No. 09/982,274, Response to Office Action Jan. 22, 2008.
U.S. Appl. No. 09/982,274, Response to Office Action Aug. 6, 2008.
U.S. Appl. No. 09/982,274, Response to Office Action Feb. 17, 2009.
U.S. Appl. No. 09/982,274, Notice of Appeal filed Sep. 9, 2009.
U.S. Appl. No. 09/982,274, Appeal Brief Filed Nov. 9, 2009.
U.S. Appl. No. 09/982,274, Reply Brief filed Apr. 2, 2010.
U.S. Appl. No. 12/112,165, filed Apr. 30, 2001.
U.S. Appl. No. 10/251,120, filed Sep. 20, 2002.
U.S. Appl. No. 10/251,120, Final Rejection Dec. 31, 2007.
U.S. Appl. No. 10/251,120, Final Rejection Jun. 25, 2009.
U.S. Appl. No. 10/251,120, Non-Final Rejection Mar. 29, 2007.
U.S. Appl. No. 10/251,120, Non-Final Rejection Jan. 5, 2009.
U.S. Appl. No. 10/251,120, Examiner Summary Oct. 21, 2009.
U.S. Appl. No. 10/251,120, Examiner Summary Jul. 6, 2010.
U.S. Appl. No. 10/251,120, Response to Office Action Sep. 28, 2007.
U.S. Appl. No. 10/251,120, Response to Office Action Oct. 7, 2008.
U.S. Appl. No. 10/251,120, Response to Office Action Apr. 6, 2009.
U.S. Appl. No. 10/251,120, Appeal Brief Filed Mar. 24, 2010.
U.S. Appl. No. 12/122,549, filed May 16, 2008.
U.S. Appl. No. 11/198,206, filed Aug. 5, 2005.
U.S. Appl. No. 11/198,206, Final Rejection Jan. 23, 2009.
U.S. Appl. No. 11/198,206, Non-Final Rejection Jun. 30, 2008.
U.S. Appl. No. 11/198,206, Response to Office Action Oct. 30, 2008.
U.S. Appl. No. 12/333,465, filed Dec. 12, 2008.
U.S. Appl. No. 12/262,266, filed Oct. 31, 2008.
U.S. Appl. No. 12/303,388, filed Dec. 4, 2008.
U.S. Appl. No. 12/303,391, filed Dec. 4, 2008.
U.S. Appl. No. 12/303,395, filed Dec. 4, 2008.
U.S. Appl. No. 12/303,399, filed Dec. 4, 2008.
U.S. Appl. No. 12/441,447, filed Mar. 16, 2009.
U.S. Appl. No. 10/344,176, filed Aug. 15, 2003.

U.S. Appl. No. 10/344,176, Final Rejection Oct. 30, 2008.
U.S. Appl. No. 10/344,176, Final Rejection Mar. 2, 2010.
U.S. Appl. No. 10/344,176, Response to Office Action Nov. 9, 2009.
U.S. Appl. No. 11/189,647, filed Jul. 26, 2005.
U.S. Appl. No. 11/189,647, Final Rejection May 11, 2010.
U.S. Appl. No. 11/189,647, Non-Final Rejection Aug. 14, 2009.
U.S. Appl. No. 11/189,647, Response to Office Action Feb. 15, 2010.
U.S. Appl. No. 10/819,256, filed Apr. 6, 2004.
U.S. Appl. No. 10/819,256, Final Rejection Jan. 6, 2009.
U.S. Appl. No. 10/819,256, Non-Final Rejection Mar. 18, 2008.
U.S. Appl. No. 10/819,256, Response to Office Action Sep. 18, 2008.
U.S. Appl. No. 11/097,947, filed Apr. 1, 2006.
U.S. Appl. No. 11/097,947, Non-Final Rejection Nov. 10, 2009.
U.S. Appl. No. 11/097,947, Final Rejection Jun. 7, 2010.
U.S. Appl. No. 11/097,947, Response to Office Action Mar. 10, 2010.
U.S. Appl. No. 10/818,574, filed Apr. 6, 2004.
U.S. Appl. No. 10/818,574, Non-Final Rejection Feb. 4, 2009.
U.S. Appl. No. 10/818,574, Response to Office Action May 4, 2009.
U.S. Appl. No. 11/074,453, filed Mar. 8, 2005.
U.S. Appl. No. 11/074,453, Non-Final Rejection Mar. 4, 2009.
U.S. Appl. No. 11/074,453, Requirement for Election Mar. 31, 2010.
U.S. Appl. No. 11/074,453, Notice of Non-compliant response Nov. 9, 2009.
U.S. Appl. No. 11/074,453, Response to Office Action Apr. 29, 2010.
U.S. Appl. No. 11/074,453, Response to Office Action Nov. 23, 2009.
U.S. Appl. No. 11/074,453, Response to Office Action Jul. 6, 2009.
U.S. Appl. No. 11/794,830, filed Jan. 22, 2008.
U.S. Appl. No. 11/794,830, Final Rejection Dec. 7, 2009.
U.S. Appl. No. 11/794,830, Non-Final Rejection May 27, 2009.
U.S. Appl. No. 11/794,830, Response to Office Action Sep. 28, 2009.
U.S. Appl. No. 11/794,830, Response to Office Action Apr. 7, 2010.
U.S. Appl. No. 11/903,607, filed Sep. 24, 2007.
U.S. Appl. No. 11/903,607, Final Rejection Jan. 28, 2010.
U.S. Appl. No. 11/903,607, Non-Final Rejection May 13, 2009.
U.S. Appl. No. 11/903,607, Response to Office Action Aug. 12, 2009.
U.S. Appl. No. 11/903,607, Response to Office Action Apr. 28, 2010.
U.S. Appl. No. 12/442,549, filed Mar. 24, 2009.
U.S. Appl. No. 12/477,179, filed Jun. 3, 2009.
U.S. Appl. No. 12/477,208, filed Jun. 3, 2009.
U.S. Appl. No. 12/477,213, filed Jun. 3, 2009.
U.S. Appl. No. 12/477,225, filed Jun. 3, 2009.
U.S. Appl. No. 12/477,189, filed Jun. 3, 2009.
U.S. Appl. No. 12/721,619, filed Mar. 11, 2010.
U.S. Appl. No. 11/715,181, filed Mar. 7, 2007.
U.S. Appl. No. 11/715,181, Non-Final Rejection Nov. 3, 2009.
U.S. Appl. No. 11/715,181, Non-Final Rejection May 12, 2010.
U.S. Appl. No. 11/715,181, Response to Office Action Feb. 3, 2010.
Rintelman, Mary Jane, "Choice and cost-savings", Credit Union Management, vol. 19, No. 7, pp. 48, 50. Jul. 1996.
Woodard, Kathy, "stay healthy for real fun—and profit", Business First Columbus, vol. 12, No. 19, S.1, p. 13. Jan. 1996.
Spencer, Peter L., "New plan cuts health car costs in half (advantage of health care plan with high deductible)", Consumers' Research Magazine, vol. 76, No. 10, pp. 16. Oct. 1993.
Communuity Hearth Health Programs: Components, Ratio: John P. Elder, Thomas L. Schmid, Phyillis Dower and Sonja Hedlund; Journal of Public Health Policy; Palgrave Macmillian; 1993 winter; pp. 463-479.
Ferling ("New plans, New policies," Ferling, Rhona. Best's Review; Apr. 1993 p. 78).
"Plan Highlights for El Paso ISD" Salary Protection Insurance Plan, web-site—http://w3.unumprovident.com/enroll/elpasoisd/your_plan.htm, Mar. 3, 2008.
Consumer-Driven Health Plans Catch on as Myths Fall by Wayside (Sep. 4). PR Newswire, 1.
Art Technology Group; Discovery Holdings to exploit online interest in healthcare and life assurance with ATG commerce functionality; Revenue potential significant as 70% of Discovery members access the internet. (Oct. 28). M2 Presswire, 1.
"Absenteeism Control"; Cole, Thomas C. et al; Management Decision; London: 1992. vol. 20, Iss. 2; p. 12 (AC).

Saleem, Haneefa: "Health Spending Accounts"; Dec. 19, 2003; posted online at http://www.bls.gov/opub/cwc/print/cm20031022ar01p1.htm.
Insure.com; "The lowdown on life insurance medical exams"; Jun. 28, 2006; Imaged from the Internet Archive Waybackmachine on May 10, 2006 at http://web.archive.org/web/20060628231712/http://articles.moneycentral.msn.com/Insurance/Insureyourlife/thelowdownonlifeinsurancwemedicalexams.aspx.
Definition of insurance, New Penguin Business Dictionary, Retrieved Oct. 26, 2008 from http://www.credoreference.com/entry/6892512/.
International Search Report for PCT/IB05/003842 filed Dec. 21, 2005 (WO2006/072822).
Written Opinion for PCT/IB05/003842 filed Dec. 21, 2005 (WO2006/072822).
International Preliminary Report on Patentability for PCT/IB05/003842 filed Dec. 21, 2005 (WO2006/072822).
International Search Report for PCT/IB07/051945 filed May 23, 2007 (WO2007/141695).
Written Opinion for PCT/IB07/051945 filed May 23, 2007 (WO2007/141695).
International Preliminary Report on Patentability for PCT/IB07/051945 filed May 23, 2007 (WO2007/141695).
International Search Report for PCT/IB07/051946 filed May 23, 2007 (WO2007/141696).
Written Opinion for PCT/IB07/051946 filed May 23, 2007 (WO2007/141696).
International Preliminary Report on Patentability for PCT/IB07/051946 filed May 23, 2007 (WO2007/141696).
International Search Report for PCT/IB07/051947 filed May 23, 2007 (WO2007/141697).
Written Opinion for PCT/IB07/051947 filed May 23, 2007 (WO2007/141697).
International Preliminary Report on Patentability for PCT/IB07/051947 filed May 23, 2007 (WO2007/141697).
International Search Report published April 23, 2009 for PCT/IB07/051948 filed May 23, 2007 (WO2007/141698).
Written Opinion published March 13, 2009 PCT/IB071051948 filed May 23, 2007 (WO2007/141698).
International Preliminary Report on Patentability published Mar. 17, 2009 for PCT/IB07/051948 filed May 23, 2007 (WO2007/141698).
International Search Report for PCT/IB07/053906 filed Sep. 26, 2007 (WO2008/038232).
Written Opinion for PCT/IB07/053906 filed Sep. 26, 2007 (WO2008/038232).
International Preliminary Report on Patentability for PCT/IB07/053906 filed Sep. 26, 2007 (WO2008/038232).
International Search Report for PCT/IB01/01406 filed Aug. 8, 2001 (WO2002/013438).
International Preliminary Report on Patentability for PCT/IB01/01406 filed Aug. 8, 2001 (WO2002/013438).
International Search Report for PCT/IB2007/053760 filed Sep. 18, 2007 (WO2008/035280).
Written Opinion for PCT/IB2007/053760 filed Sep. 18, 2007 (WO2008/035280).
International Preliminary Report on Patentability for PCT/IB2007/053760 filed Sep. 18, 2007 (WO2008/035280).
Andrew Cohen; Putting Wellness to work; date Mar. 1, 1997; Athletic Business, pp. 1-7.
www.netpulse.net; Netpulsue Makes Working Out More than a Calorie-Burning Session; date Mar. 21, 1998, pp. 1-2.
www.netpulse.net; 24 Hour Fitness Partners with Netpulse; date Mar. 9, 1998; p. 1.
Trends in Medical Benefit Plan Design to Control Claim Costs; Record of Society of Actuaries; date 1982; vol. 8, No. 2, pp. 515-531.
David Richards, Return of Premium Disability Insurance; The Black Hole, dated Jul. 15, 2010, p. 1-4.
002 Co-pending U.S. Appl. No. 09/876,311, Non-final Office Action mailed Jul. 9, 2010.
019 Co-pending U.S. Appl. No. 11/074,453, Final Office Action mailed Jul. 19, 2010.
015 Co-pending U.S. Appl. No. 11/189,647, Request for Continued Examination filed Jul. 19, 2010.

021 Co-pending U.S. Appl. No. 11/715,181, Response filed Aug. 12, 2010.
003-1 Co-pending U.S. Appl. No. 12/112,165, Non-final Office Action mailed Sep. 2, 2010.
004 co-pending U.S. Appl. No. 10/251,120, Request for Continued Examination filed Oct. 6, 2010.
U.S. Appl. No. 11/074,453, Response to final office action Dec. 20, 2010.
U.S. Appl. No. 12/303,395 Non-Final Rejection Jan. 24, 2011.

U.S. Appl. No. 12/303,388 Non-final Office Action Mar. 11, 2011.
U.S. Appl. No. 11/715,181, Response to Office Action Mar. 11, 2011.
U.S. Appl. No. 12/112,165, Final Office Action Feb. 10, 2011.
U.S. Appl. No. 12/477,225, Non-final Office Action Mar. 25, 2011.
U.S. Appl. No. 12/333,465, Non-final Office Action Mar. 30, 2011.
U.S. Appl. No. 12/122,549, Non-final Office Action Mar. 30, 2011.

* cited by examiner

METHOD OF INCENTIVISING MEMBERS OF A DISEASE MANAGEMENT PROGRAMME TO COMPLY WITH THE PROGRAMME

BACKGROUND OF THE INVENTION

This invention relates to a method of incentivising members of a disease management programme to comply with the programme.

Known disease management programmes typically face the major problem of poor patient compliance with an enforced, funder driven programme.

It is therefore an objective of the present invention to provide a method of incentivising members of a disease management programme to comply with the programme in order to address this problem. This effectively changes the programme from a supply side "push" to a demand side "pull" programme.

SUMMARY OF THE INVENTION

According to a first embodiment of the present invention, there is provided a method of incentivising members of a disease management programme to comply with the programme, the method comprising the steps of:
- defining a plurality of general programme areas and a plurality of specific programme areas;
- associating each of the plurality of general programme areas with each of the diseases managed by the programme;
- associating each of the plurality of specific programme areas only with those diseases managed by the programme to which the specific programme area is determined to be of particular benefit to a member afflicted with the disease;
- awarding points to a member for each of the programme areas in which the member participates, only if the member is afflicted with a disease which is associated with that particular programme area; and
- allocating a reward to the member if the points awarded to the member accumulate to a predetermined amount.

Preferably, points are only awarded to the member if the member participates in all of the programme areas which are associated with the disease or diseases with which the member is afflicted.

Alternatively, additional points are awarded to the member if the member participates in all of the programme areas which are associated with the disease or diseases with which the member is afflicted.

The general programme areas may be diet, exercise, smoking and education.

The specific programme areas may be blood pressure, flow volume loop measurement, influenza vaccine, pneumococcal vaccine, cholesterol and long term glucose control.

The method may further include the steps of:
- defining a measurable within at least one of the general and/or specific programme areas so that a members performance within said programme area can be ascertained;
- defining a minimum level of the measurable, which minimum level indicates a minimum required level of member performance within the at least one programme area; and
- awarding points to a member if the member obtains the defined minimum level of a measurable for the at least one programme area only if the member is afflicted with a disease which is associated with that particular programme area.

The method may also include the step of awarding additional points to the member if the member obtains the minimum level of a measurable for all of the programme areas which are associated with the disease with which the member is afflicted.

According to a second embodiment of the present invention there is provided a method of incentivising members of a disease management programme to comply with the programme, the method comprising the steps of:
- defining a plurality of general programme areas and a plurality of specific programme areas;
- associating each of the plurality of general programme areas with each of the diseases managed by the programme;
- associating each of the plurality of specific programme areas only with those diseases managed by the programme to which the specific programme area is determined to be of particular benefit to a member afflicted with the disease;
- defining a measurable within each of the general and specific programme areas so that a member's performance within said programme area can be ascertained;
- defining a minimum level for each measurable, which minimum level indicates a minimum required level of member performance within each of the programme areas;
- awarding points to a member if the member obtains the minimum level of a measurable for a particular programme area only if the member is afflicted with a disease which is associated with that particular programme area; and
- allocating a reward to the member if the points awarded to the member accumulate to a predetermined amount.

Additional points are preferably awarded to the member if they obtain the minimum level of a measurable for all of the programme areas which are associated with the disease with which the member is afflicted.

According to the present invention there is further provided a method of incentivising members of a disease management programme to comply with the programme, the method comprising the steps of:
- defining a plurality of general programme areas and a plurality of specific programme areas;
- associating each of the plurality of general programme areas with each of the diseases managed by the programme;
- associating each of the plurality of specific programme areas only with those diseases managed by the programme to which the specific programme area is determined to be of particular benefit to a member who is predisposed to being afflicted with the disease;
- awarding points to a member for each of the programme areas in which the member participates, only if the member is predisposed to being afflicted with a disease which is associated with that particular programme area; and
- allocating a reward to the member if the points awarded to the member accumulate to a predetermined amount.

According to the present invention there is still further provided a method of incentivising members of a disease management programme to comply with the programme, the method comprising the steps of:
- defining a plurality of general programme areas and a plurality of specific programme areas;

associating each of the plurality of general programme areas with each of the diseases managed by the programme;
associating each of the plurality of specific programme areas only with those diseases managed by the programme to which the specific programme area is determined to be of particular benefit to a member who is predisposed to being afflicted with the disease;
defining a measurable within each of the general and specific programme areas so that a member's performance within said programme area can be ascertained;

According to the invention, a plurality of general programme areas and specific programme areas are defined. Each of the diseases managed by the programme are associated with each one of the general programme areas, while the specific programme areas are only associated with those diseases managed by the programme to which they would be of particular benefit to a person stricken by that disease.

For the illustrative diseases of the present invention, the table below shows the general and specific programme areas:

DESCRIPTION OF THE PROGRAMME

| | General | | | | Specific | | | | | |
|---|---|---|---|---|---|---|---|---|---|---|
| | Diet | Exercise | Smoking | Education | Blood Pressure | FlowVol Loop | Flu vaccine | Pneumo vaccine | Cholesterol | Long term glucose control |
| Hyper-Tension | ✓ | ✓ | ✓ | ✓ | ✓ | | | | ✓ | |
| Asthma | ✓ | ✓ | ✓ | ✓ | | ✓ | ✓ | ✓ | | |
| Hyper-lipidaemia | ✓ | ✓ | ✓ | ✓ | | | | | ✓ | |
| COPD | ✓ | ✓ | ✓ | ✓ | | ✓ | ✓ | ✓ | | |
| Diabetes Mellitus | ✓ | ✓ | ✓ | ✓ | ✓ | | | | ✓ | ✓ | defining a minimum level for each measurable, which minimum level indicates a minimum required level of member performance within each of the programme areas;
awarding points to a member if the member obtains the minimum level of a measurable for a particular programme area only if the member is predisposed to being afflicted with a disease which is associated with that particular programme area; and
allocating a reward to the member if the points awarded to the member accumulate to a predetermined amount.

DESCRIPTION OF AN EMBODIMENT

According to the present invention, people suffering from one or more of a list of predetermined diseases qualify to become members of the disease management programme of the present invention.

For illustrative purposes, the invention will be described with reference to the following conditions:
1. Hypertension.
2. Diabetes Mellitus.
3. Hyperlipidaemia.
4. Asthma.
5. Chronic Obstructive Pulmonary Disease (COPD).

It will be appreciated that the method of the present invention could be equally applied to any other disease or condition, and is particularly suitable for any other type of chronic disease.

It will once again be appreciated that the general and specific programme areas selected could include other general or specific programme areas if these were found to be particularly beneficial to a person stricken with a disease managed by the programme.

Furthermore, if it was found that one of the general or specific programme areas were not particularly beneficial to a person stricken with the disease, these could be removed from the programme, either altogether or for a particular disease only.

It is obvious that these programme areas may be relevant even to a person not stricken with one of the illustrated diseases. However, a programme area is only linked to a disease if there is some particular advantage that the programme area would have for a person afflicted with the disease over and above the advantage the programme area would have for a person not afflicted with the disease.

Referring to the above table, and using hypertension as an example, all the general programme areas of diet, exercise, smoking and education are important for the disease management of a person with hypertension.

Furthermore, the specific programme areas of blood pressure measurements and cholesterol are important to a person with hypertension. However, flow volume loop, an influenza vaccine, a pneumococcal vaccine and long term glucose control are not of particular importance to a person with hypertension only.

For each one of the diseases managed by the programme, a member of the programme will be awarded points either for participating in a relevant programme area and/or for complying with a required level of performance within the programme area only if the member is afflicted with a disease which is associated with that particular programme area. The points allocation will be described in more detail below.

Thus, a person afflicted with hypertension is awarded points for complying with a required level of performance within the programme areas of diet, exercise, smoking, education, blood pressure and cholesterol, but will not be awarded points for participating and/or complying with a required level of performance within the programme areas of flow volume loop and long term glucose control, unless the person also suffers from another disease which may have these areas associated.

It is obviously important that each of the programme areas have measurables by means of which it is possible to test whether a member of the programme is complying with a required level of performance for that particular programme area.

For the general programme area of "diet", three possible measurables are the body mass index, the percentage body fat of the member or a goal weight certificate from an accredited weight organisation such as Weigh-Less™.

A minimum level of performance is achieved if a member's body mass index or percentage body fat result is within the acceptable range depending on the member's age and gender, or if the member obtains a goal weight certificate, for example, from Weigh-Less, at one point in the year.

The measurable for the general programme area of "exercise" is two fitness assessments per year, at least five months apart. The member will have complied with the minimum acceptable level if they maintain at least a predetermined level of fitness. If a member's disease prohibits them from obtaining the required fitness level, as may be the case with COPD or any another physical impairment, this should be taken into account by the fitness assessor.

The measurable for the general programme area of "smoking" is a urine cotinine test, with the obvious minimum level of performance being that the test must be negative.

It is also possible to perform the urine cotinine test on a random selection of members. However, because it is essential that patients with hypertension, hyperlipidaemia, diabetes mellitus, asthma and COPD do not smoke, this test should be performed on all members with these chronic illnesses.

The measurable for the general programme area of "education" is a questionnaire prepared by the managers of the disease management programme. Members need only complete the questionnaire once off and thereafter at the discretion of the managers of the disease management programme. The minimum level of performance is merely that the member completes the questionnaire either on-line using a computer or on a paper copy, both of which provide the correct answers to the questions, thereby educating the member.

Turning now to the specific programme areas, the measurable for "blood pressure" is two blood pressure measurements per year, at least five months apart.

A typical minimum acceptable level for the blood pressure measurements is equal to or less than 140/90 mmHg (less than 130/85 mmHg in diabetic patients).

The measurable for "flow volume loop" is 2 flow volume loop measurements per year, at least five months apart. A typical minimum acceptable level for Asthma patients is as follows:

| |
|---|
| $FEV_1 > 80\%$ predicted |
| $FVC > 80\%$ predicted |
| $TLCO > 80\%$ predicted |
| $FEV_1/FVC > 75\%$ predicted |

As COPD is not reversible, there is no minimum acceptable level for a COPD patient.

The measurable for the "influenza vaccine" is one approved vaccination per year between 1 March and 30 April when the programme is managed in the Southern Hemisphere. In this case, the minimum acceptable level is equal to merely performing in this programme area.

The measurable for the specific programme area of "pneumococcal vaccine" is once every five years for high-risk patients.

The measurable for the specific programme area of "cholesterol" is a fasting cholesterol test, once a year for members with hyperlipidaemia, hypertension and diabetes mellitus. The following are the minimum acceptable levels:

| Cholesterol | Level |
|---|---|
| Total | <5.3 mmol/L |
| LDL-C | <3.4 mmol/L |
| HDL-C | >1 mmol/L |

The measurable for the specific programme area of "long term glucose control" is an HbA1 c test which is a glycosylated haemaglobin test which measures the patient's glucose control during the preceding three months. A member must obtain two measurements per year, at least five months apart. An acceptable minimum level is a test result of 7% or less.

Turning now to the points allocation, according to the present invention the points are allocated to members based on a multi-level system. On the first level, a member is awarded points for merely taking part in a programme area associated with their disease. Thus a member merely going for a fitness assessment will be awarded points regardless of the results of the assessment.

Where a member is afflicted with more than one disease, they will be awarded points for taking part in a programme area associated with any of their diseases. Where a programme area is associated with more than one disease, the member will only be awarded points once for taking part in that programme area.

The second level of the points allocation system is that a member will be awarded an even greater number of points for taking part in all of the programme areas associated with the disease with which the member is afflicted. This is because it is more important for members to take part in all of the programme areas than if they were only to take part in some of the programme areas. Thus, the points are awarded so that a member obtains compliance points for participating in all of the programme areas. It will be appreciated that the points allocation could be set up so that a member only gets allocated points if they participate in all of the programme areas.

Where a member is afflicted with more than one disease, they will have to take part in all of the programme areas associated with all of the diseases with which the member is afflicted to obtain their level two compliance points.

The third level of points allocation occurs if the member actually attains a minimum level for a measurable of a programme area associated with their disease or diseases. Thus, it is not merely the member's participation in the programme area which is required, but the member must attain an acceptable minimum level within that programme area before they will be awarded points.

Once again, where a member is afflicted with more than one disease, they will be awarded points for obtaining an acceptable minimum level within a programme area associated with any of their diseases. Where a programme area is associated with more than one disease, the member will only be awarded points once for taking part in that programme area.

For some diseases, the acceptable minimum level is more stringent than for others to obtain level three target points. Thus a member afflicted with more than one disease must meet the most stringent acceptable minimum level to obtain these points.

The final level of points allocation is if the member attains the acceptable minimum level for a measurable in all of the programme areas associated with their disease or diseases.

As with level two, where a member is afflicted with more than one disease, they will have to attain the acceptable minimum level for a measurable in all of the programme areas associated with all of their diseases to obtain their level four bonus points.

It will be appreciated that the present invention can be implemented using the points allocation of all of the above-mentioned levels, or the present invention can be implemented using a combination of only some of these levels.

The prototype of the present invention was implemented using the first, second and third levels.

For example, a member who has hypertension earns first level points by participating in the general and specific programme areas associated with the disease.

In the prototype, these points are as follows:

| |
|---|
| Diet - 5000 |
| Exercise - 15 000 |
| Smoking - 5 000 |
| Education - 1 000 |
| Blood Pressure - 1 000 |
| Cholesterol - 2 000 |

For participating in all of the programme areas associated with a disease, a member will typically obtain the above points together with an additional 4 000 compliance points. This is the second level of the points allocation system.

Thus, if the member is not at goal weight, goal BMI or goal percentage body fat, then the member has to be enrolled in a weigh-less programme. If the member is a smoker, they would have to be enrolled in a smoke enders programme.

On the next level of the points allocation, the member is awarded 600 target points for achieving the minimum level within each programme area, as described above. Thus, a member with hypertension is able to earn 3 600 extra target points in total on this level, while a member with Diabetes Mellitus is able to earn an extra 5 400 target points on this level.

Finally, if the member achieves the minimum levels for all of the programme areas for a particular disease, the member is awarded another suitable amount of bonus points. This level was not implemented in the prototype of the invention, but is an obvious extension of the prototype of the invention.

Once the points awarded to a member accumulate to a predetermined amount, the member is rewarded in an appropriate way. The reward may be a cash payout, special options on services such as aeroplane tickets, hotel accommodation and/or car rentals or any other appropriate reward. The amount of the reward is related to the amount of points accumulated by the member, so the more points a member accumulates the more they are rewarded.

Thus it will be appreciated that the present invention incentivises members to comply with the disease management programme.

It will also be appreciated that the present invention could be applied where the members of the programme do not yet have a disease, but are identified as being predisposed to being afflicted by a particular disease, for example by being in a high risk group for the disease. In this case, by being incentivised to comply with the programme, the member's health is protected thereby hopefully preventing them from contracting the disease.

Furthermore, the present invention could equally be applied to incentivise doctors to help their patients comply with the programme. Thus, a doctor whose patient obtains points for any of the various levels could also be awarded points, thus incentivising the doctor to further encourage the patient to comply with the programme.

We claim:

1. A method of incentivising members of a disease management programme to comply with the programme, using a computer, the method comprising the steps of:

inputting into the computer data definitions of a plurality of general programme areas and a plurality of specific programme areas, wherein the plurality of general programme areas are programme areas that if complied with are of benefit to a member stricken with any disease managed by the disease management programme and wherein the plurality of specific programme areas are programme areas that are determined to be of particular benefit to a member afflicted with some but not all of the diseases managed by the disease management programme;

calculating, using the computer, an award of points to a member for each of the general programme areas in which the member participates, the points being allocated to members based on a multi-level system, including:

a first level, wherein the member is awarded points for merely taking part in a programme area, a second level, wherein the member is awarded a bonus set of points in addition to the points awarded in the first level in response to participating in all programme areas associated with a disease with which the member is afflicted, and a third level, wherein the member is awarded points for attaining a minimum level for a measurable of a programme area associated with a disease with which the member is afflicted;

inputting into the computer a definition of a measurable within each of the general and specific programme areas so that a member's performance within said programme area can be ascertained;

inputting into the computer a minimum level for each measurable, which minimum level indicates a minimum required level of member performance within each of the programme areas;

calculating, using the computer, an award of points to a member for each of the specific programme areas in which the member participates, only if the member is afflicted with a disease to which the specific programme area in which the member participates has been determined to be of particular benefit and if the member obtains the minimum level of a measurable for a particular programme area;

calculating, using the computer, a total number of points awarded to the member; and calculating, using the computer, an allocation of a reward to the member if the total number of points awarded to the member accumulates to a predetermined amount of points.

2. A method according to claim 1, wherein points are only awarded to the member if the member participates in all the programme areas which are associated with the disease or diseases with which the member is afflicted.

3. A method according to claim 1, wherein additional points are awarded to the member if the member participates in all of the programme areas which are associated with the disease or diseases with which the member is afflicted.

4. A method according to claim 1, wherein the general programme areas are some of diet, exercise, smoking and education.

5. A method according to claim 1, wherein the specific programme areas are one or more of blood pressure, flow volume loop measurement, influenza vaccine, pneumococcal vaccine, cholesterol and long term glucose control.

6. A method according to claim 1 wherein, additional points are awarded to the member if they obtain the minimum level of a measurable for all of the programme areas which are associated with the disease with which the member is afflicted.

7. A method according to claim 1, wherein the amount of the reward is related to the amount of points accumulated by the member.

8. A method according to claim 1, wherein the reward is a cash payout or special options on services.

9. A method according to claim 8, wherein the services are one or more of airplane tickets, hotel accommodation and car rentals.

* * * * *